(12) United States Patent
Streffer

(10) Patent No.: US 8,895,290 B2
(45) Date of Patent: Nov. 25, 2014

(54) METHOD FOR DIGESTING A BIOMASS COMPRISING LIGNIN TOGETHER WITH CELLULOSE AND/OR HEMICELLULOSE

(75) Inventor: Friedrich Streffer, Berlin (DE)

(73) Assignee: Maxbiogas GmbH, Marienwerder (DE)

(*) Notice: Subject to any disclaimer, the term of this patent is extended or adjusted under 35 U.S.C. 154(b) by 21 days.

(21) Appl. No.: 13/124,306

(22) PCT Filed: Oct. 16, 2009

(86) PCT No.: PCT/EP2009/007583
§ 371 (c)(1),
(2), (4) Date: Apr. 14, 2011

(87) PCT Pub. No.: WO2010/043424
PCT Pub. Date: Apr. 22, 2010

(65) Prior Publication Data
US 2011/0201096 A1     Aug. 18, 2011

(30) Foreign Application Priority Data

Oct. 17, 2008 (EP) .................................. 08018248
Aug. 28, 2009 (EP) .................................. 09011072

(51) Int. Cl.
*C08H 8/00*                (2010.01)

(52) U.S. Cl.
CPC *C08H 8/00* (2013.01); *Y02E 50/343* (2013.01)
USPC ............................................................. 435/277

(58) Field of Classification Search
USPC ............................................................. 435/277
See application file for complete search history.

(56) References Cited

U.S. PATENT DOCUMENTS

| | | | |
|---|---|---|---|
| 2,024,689 A * | 12/1935 | Groombridge et al. | 162/77 |
| 2,541,059 A | 2/1951 | Heritage et al. | |
| 3,251,820 A | 5/1966 | Grangaard | |
| 3,423,395 A | 1/1969 | Quimby et al. | |
| 4,111,928 A * | 9/1978 | Holsopple et al. | 530/507 |
| 7,452,466 B2 * | 11/2008 | Binning et al. | 210/603 |
| 2003/0041982 A1 | 3/2003 | Prior | |
| 2004/0121436 A1 | 6/2004 | Blount | |
| 2007/0215300 A1 * | 9/2007 | Upfal et al. | 162/29 |

FOREIGN PATENT DOCUMENTS

| | | | | |
|---|---|---|---|---|
| DE | 2365480 | 5/1975 | | |
| FR | 1547560 | 11/1968 | | |
| WO | WO9814270 | 4/1998 | | |
| WO | WO0132715 A1 | 5/2001 | | |
| WO | WO03025280 A1 | 3/2003 | | |
| WO | WO2005017001 A1 | 2/2005 | | |
| WO | WO2005053812 A1 | 6/2005 | | |
| WO | WO2006086861 | * | 8/2006 | ............... C08H 5/04 |
| WO | WO2006086861 A2 | 8/2006 | | |
| WO | WO2008043837 | * | 4/2008 | ................. C08J 3/09 |

OTHER PUBLICATIONS

Merriam Webster Dictionary. Fermentation. 2012.*
PubChem Compound. Propyl Ether. 2012.*
PubChem Compound. Diisopropyl Ether. 2012.*
Zhang et al. Fractionating recalcitrant lignocellulose at modest reaction conditions. Biotechnology and Bioengineering. 2007;97(2):214-223.*
International Search Report corresponding to International Application No. PCT/EP2009/007583 dated Nov. 26, 2009 and mailed Apr. 12, 2009.
Written Opinion of the International Searching Authority corresponding to International Application No. PCT/EP2009/007583 dated Dec. 7, 2009.
US Patent 3,423,395 corresponds to FR1547560, Jan. 21, 1969.

* cited by examiner

*Primary Examiner* — Ruth Davis
*Assistant Examiner* — Lynn Y Fan
(74) *Attorney, Agent, or Firm* — F. Chau & Associates, LLC

(57) ABSTRACT

The invention relates to a method for digesting a biomass comprising, lignin, cellulose, and hemicellulose, comprising the steps of: (a) contacting the biomass with a first solvent for dissolving the cellulose and/or the hemicellulose, (b) contacting the dissolved cellulose and/or hemicellulose with a precipitant for forming a precipitate comprising cellulose and/or hemicellulose and residual lignin, wherein the precipitant is selected from the group consisting of alkanes, ethers, and esters; and (c) contacting the precipitate with a second solvent for removing residual lignin from the precipitate. The invention further relates to an apparatus for performing such a method.

11 Claims, 3 Drawing Sheets

METHOD FOR DIGESTING A BIOMASS COMPRISING LIGNIN TOGETHER WITH CELLULOSE AND/OR HEMICELLULOSE

CROSS-REFERENCE TO RELATED APPLICATION

This application is a National Stage application under 35 U.S.C. 371 which claims priority to International PCT Application No. PCT/EP2009/007583, filed on Oct. 16, 2009, the disclosure of which is hereby incorporated by reference herein in its entirety.

The present invention relates to a method for digesting a biomass comprising lignin, together with cellulose and/or hemicellulose. According to this method, the lignocellulose containing biomass is fractionated to separate the lignin from the carbohydrates which can subsequently be fermented efficiently to useful products like methane (biogas), hydrogen, ethanol, acetone, butanol, and/or iso-propanol. This method allows using lignocellulose as a new class of cost efficient substrates for efficient fermentation processes. The invention further relates to an apparatus for performing such a method.

INTRODUCTION

Pulping processes have previously been used to separate cellulose from lignin and other components of lignocellulose containing materials. For example, various types of inorganic chemicals in water have been used to modify lignin to render it water soluble. Those processes present a problem in recovering or destroying the inorganic chemicals.

Other processes have been proposed using organic solvents for dissolving the lignin from the lignocellulose containing material. Such processes have been expensive due to the high costs of the necessary solvent recovery.

Still other processes have involved a combination of acids and alcohols with water. However, the presence of excess water can be detrimental to the process due to costly recovery systems.

In addition, the high temperatures of many known processes trigger a reaction of hemicellulose to furfural inhibiting the enzymes and microorganisms of the following fermentation which demands laborious and expensive detoxification.

In summary, many methods known in the state of the art are costly and show difficulties in the recovery of the solvent which might entail laborious method steps such as separating different solvents using centrifugation or detoxification.

SHORT DESCRIPTION OF THE INVENTION

Accordingly, the problem underlying the present invention was to provide a method for digesting a biomass comprising lignin together with cellulose and/or hemicellulose (lignocellulose containing biomass) that is cheap and can be performed without the need of expensive equipment.

This problem is solved by a method according to the present invention. Briefly, such a method for digesting biomass comprising lignin together with cellulose and/or hemicellulose may comprise the following steps. First, the biomass is contacted with a first solvent for dissolving the cellulose and the hemicellulose. Secondly, the cellulose and/or the hemicellulose are precipitated by contacting it/them with a precipitant to a compact solid, wherein the precipitant that is selected from the group consisting of alkanes, ethers, and esters or a mixture of these. The precipitate formed thereby may contain low amounts of residual lignin in addition to cellulose and/or hemicellulose. Advantageously, the precipitate formed has a relatively low content of the first solvent and in particular of the precipitant, which reduces the volume of solvent needed in the following steps. Thirdly, the precipitate is contacted with a second solvent for dissolving the lignin in the precipitate. This step can also be performed when precipitating the cellulose and/or hemicellulose. Fourthly, the precipitate containing amorphous cellulose and hemicellulose may be washed with a bio-compatible third solvent to remove remaining traces of the first solvent, the precipitant and/or the second solvent. Fifthly, an aerobic or anaerobic fermentation of the cellulose, the hemicellulose, and/or the lignin may optionally be performed, e.g. biogas fermentation, alcoholic fermentation, or AB-fermentation. This fermentation includes the cleavage of the cellulose and hemicellulose to smaller sugar oligomers.

This method has the advantage of being comparatively cheap. Furthermore, it can be performed without difficult separation or recovery steps of solvents, such as those requiring phase separation and/or centrifugation. In addition, no detoxification step needs to be performed in the method of the invention.

The method of the invention can be performed as a continuous process to obtain sugars from lignocellulose containing biomass, but can also be a batch or fed batch process (see FIGS. 1 and 2). The method of the invention may be combined with an aerobic or anaerobic fermentation, in particular to prepare solvents, biogas, biofuels, and/or other chemicals.

In addition, the invention pertains to an apparatus for performing the method of the invention.

DETAILED DESCRIPTION OF THE INVENTION

Figure 1:
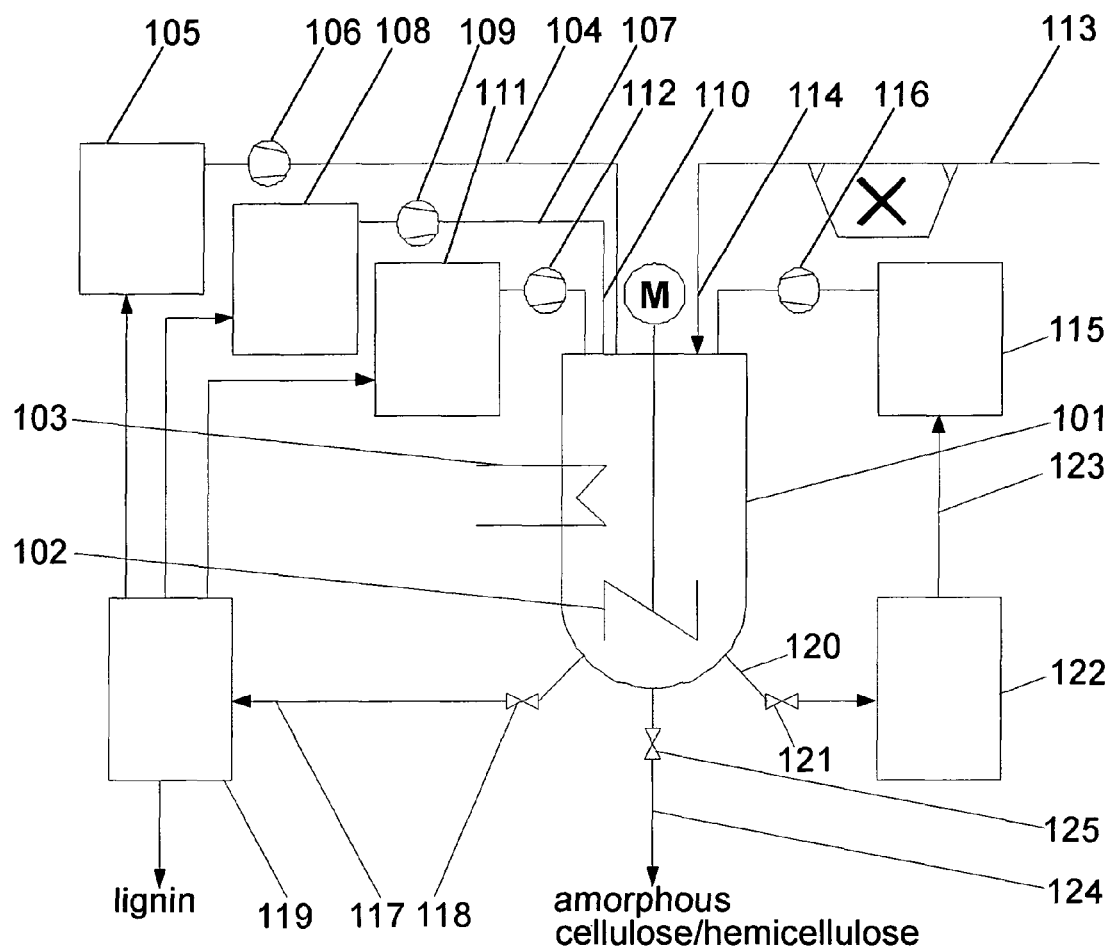
FIG. 1: Apparatus for performing the method of the invention as a batch or fed batch process. The step of introducing the second solvent can be combined with the step of introducing the precipitant (precipitation step).

The present method for digesting a biomass, comprising lignin together with cellulose and/or hemicellulose comprises the following steps:

First, the biomass is brought into contact with a first solvent for dissolving the cellulose and/or the hemicellulose. This is preferably done at a temperature below 120° C. and below a pressure of 300 kPa for less than 4 hours.

Secondly, the dissolved cellulose and/or hemicellulose are precipitated by bringing it in contact with a precipitant for forming a precipitate comprising cellulose and/or hemicellulose and residual lignin, preferably at a temperature below 120° C. and at a pressure of below 300 kPa for less than 30 min. The precipitant used in this step is selected from the group consisting of alkanes, ethers, and esters, which are described in more detail below.

Thirdly, the precipitate is contacted with a second solvent for removing residual lignin from the precipitate by dissolving it, preferably precipitate at a temperature below 120° C. and at a pressure below 300 kPa for less than 60 min. This step can also be performed together with, i.e. timely parallel to the second step of precipitating the cellulose and/or hemicellulose.

The use of an alkane, ether and/or ester as precipitant leads to a precipitate with low amounts of precipitant, i.e. with a low volume. This allows for the use of smaller amounts of solvents in the subsequent steps of the method of the invention. Therefore, the costs of the method are lower than for methods using known precipitants.

The term "digestion" or "digesting a biomass" is used herein in particular as referring to making the biomass, i.e. at least one of its components, accessible for an aerobic or anaerobic fermentation of the cellulose, the hemicellulose, and/or the lignin.

In a preferred embodiment of the invention, the method further comprising the step of contacting or mixing the precipitate containing amorphous cellulose and/or hemicellulose with a third solvent for removing residual first solvent, residual precipitant and/or residual second solvent from the precipitate. This step removes any residual substances (namely the first solvent, the precipitant and/or the second solvent) that might still be present in the precipitate, and that might negatively interfere with a possible subsequent fermentation step. Therefore, this step renders the digestion products to be bio-compatible. This step is preferably performed at a temperature below 120° C. and at a pressure of below 300 kPa for less than 60 min.

Optionally, in a further preferred embodiment of the invention, the method additionally comprises the step of contacting or mixing the precipitate with a fourth solvent, which may be water or a buffer solution like a citrate solution, a phosphate solution, a HEPES solution, a Tris solution, a MOPS solution or a similar solution for dissolving and/or suspending the cellulose and/or hemicellulose. This step is preferably performed at a temperature below 100° C. for less than 60 min. Subsequently, an aerobic or anaerobic fermentation of the cellulose, the hemicellulose, and/or the lignin may be performed using at least one microorganism, in particular at least one bacteria or at least one yeast, for fermenting the pentoses and hexoses obtained by the present method.

In the present method, it is preferred that the first solvent used is selected from the group consisting of inorganic acids, preferably sulfuric acids, hydrochloric acid, nitric acid, phosphoric acid, and polyphosphoric acid;

inorganic hydroxides, preferably potassium hydroxide, sodium hydroxide, lithium hydroxide;

organic acids, preferably formic acid, acetic acid, propionic acid, butyric acid;

ammonia, and hydrazine;

ionic solutions, preferably lithium chlorid/N,N-dimethylacetamide, lithium bromide/N,N-dimethylacetamide, 1-butyl-3-methylimidazolium hexafluorophosphate, dimethyl sulfoxide/tetrabutyl ammonium fluoride trihydrate;

solutions of at least one transition metal complex and its mixtures (preferably of two components), preferably of 1,2-ethylenediamine cadmium hydroxide (Cadoxen, $[Cd(H_2N—(CH_2)_2—NH_2)_3](OH)_2$), cuprammonium hydroxide (Cuam, $[Cu(NH_3)_4](OH)_2$), 1,2-ethylenediamine copper hydroxide (Cuen, $[Cu(H_2N—(CH_2)_2—NH_2)_2](OH)_2$), 1,3-propylenediamine copper hydroxide (Cupren, $[Cu(H_2N—(CH_2)_3—NH_2)_2](OH)_2$), 1,2-ethylenediamine palladium hydroxide (Pd-en, $[Pd(H_2N—(CH_2)_2—NH_2)](OH)_2$), 1,2-ethylenediamine cobalt hydroxide (Cooxen, $[Co(H_2N—(CH_2)_2—NH_2)_2](OH)_2$), Zincoxen, $[Zn(H_2N—(CH_2)_2—NH_2)_2](OH)_2$), nickel ammonium hydroxide (Nioxam, $[Cu(NH_3)_6](OH)_2$), 1,2-ethylenediamine nickel hydroxide (Nioxen, $[Ni(H_2N—(CH_2)_2—NH_2)_3](OH)_2$), tri-aminoethylamine nickel hydroxide (Nitren, $[Ni(NH_2CH_2CH_2)_3N](OH)_2$);

water; and a mixture of any of the beforementioned compounds.

It is preferred that the ionic solution or ionic liquid contains at least one ionic substance. Such an ionic substance can be of an annular or open-chain structure. The melting point of the substance is preferably below 100° C. The ionic liquid may contain at least one anion, such as a halogen ($Cl^-$, $Br^-$, and/or $I^-$), a carboxyalte (e.g. acetate, formate, propionate, butyrate, citrate, oxylate, and/or maleate), or a phosphonate (methylphosphonate, and/or ethyl-phosphonate) or $PF^{6-}$ or $BF^{4-}$. The ionic liquid may contain at least one cation, such as (possibly alkylated) imidazolium, (possibly alkylated) pyrazolium, (possibly alkylated) ammonium, (possibly alkylated) cholinium, (possibly alkylated) piperidinium, or (possibly alkylated) pyrrolidinium. Preferably, the ionic liquid comprises or contains 1-butyl-3-methylimidazolium bromide, 1-allyl-3-methylimidazolium cloride, N-tributyl-N-methylammonium iodide, 1-ethyl-3-methylimidazolium formate, 1-ethyl-methylimidazolium acetate, choline acetate, N,N-dimethylbutanammonium formate, and/or N-methylpiperidinium butyrate.

As a first solvent, phosphoric acid, polyphosphoric acid, Cuen, sulfuric acid, a mixture of HCl with concentrated acetic acid, or a mixture of formic acid and zinc cloride is preferred.

Preferably, the alkanes used as a precipitant are alkanes with eight C-atoms or less, more preferably selected from the group consisting of pentane, hexane, cyclo hexane, heptane, octane, and their isomers, either alone or in any mixture of the beforementioned alkanes. More preferred are the alkanes cyclopentane, hexane and cyclohexane.

The ethers used as a precipitant in the present method can be ethers with eight C-atoms or less, preferably selected from the group consisting of methyl-tert. butylether (MtB ether), ethyl-tert. butylether (EtB ether), propyl-tert. butyl ether, butyl-tert. butyl ether, dimethyl ether, methyl ethyl ether, diethyl ether, methyl propyl ether, ethyl propyl ether, methyl butyl ether, methyl pentyl ether, ethyl butyl ether, dipropyl ether, methyl hexyl ether, ethyl pentyl ether, propyl butyl ether, methyl heptyl ether, ethyl hexyl ether, propyl pentyl ether, dibutyl ether, and their isomers, either alone or in any mixture of the beforementioned ethers. More preferred ethers are Mtb ether, Etb ether, Diethyl ether and dipropyl ether.

The esters used as a precipitant are preferably esters with eight C-atoms or less, more preferably selected from the group consisting of methyl acetate, ethyl acetate, propyl acetate, butyl acetate, pentyl acetate, hexyl acetate, methyl formate, ethyl formate, propyl formate, butyl formate, pentyl formate, hexyl formate, heptyl formate, methyl propionate, ethyl propionate, propyl propionate, butyl propionate, pentyl propionate, methyl butyrate, ethyl butyrate, propyl butyrate, butyl butyrate, methyl pentanoate, ethyl pentanoate, propyl pentanoate, methyl hexanoate, ethyl hexanoate, and their isomers, either alone or in any mixture of the beforementioned esters. More preferred esters are methyl acetate, ethyl acetat, isopropyl acetate and ethyl formiate.

In a preferred embodiment of the present method, the second solvent is chosen from the group consisting of ketones with seven C-atoms or less, preferably dipropylketone, ethyl-butyl-ketone, methyl-pentyl-ketone, ethyl-propyl-ketone, methyl-butyl-ketone, diethylketone, methyl-propyl-ketone, methyl-ethyl-ketone, acetone, and isomers of the beforementioned ketones;

alcohols, preferably hexanol, pentanol, butanol, propanol, ethanol, methanol, and isomers of the beforementioned alcohols;

aldehydes, preferably hexanal, pentanal, butanal, propanal, ethanal, and isomers of the beforementioned aldehydes.

water; and a mixture of any of the beforementioned compounds.

It is more preferred that the second solvent is acetone, a mixture of acetone and water, ethanol, butanol, a mixture of ethanol and water, ethyl methyl ketone, propanal, or butanal.

In a further preferred embodiment of the present method, the third solvent is chosen from the group consisting of
water, and
hemicellulose solution, in particular saturated hemicellulose solution.

It is also preferred that the ratio of the first solvent to the biomass is preferably about 5:1 (weight/weight), but can be greater if desired. The volumetric ratio of the first solvent and the precipitant ranges preferably from 1:1 to 1:3 (volume/volume).

In the following, the use of the present method is described with regard to performing this method in suitable container, in particular a reactor (see FIGS. 1 and 2, and as described below), digesting in particular a lignocellulose containing biomass.

The method of this invention involves in one embodiment placing the biomass, in particular the lignocellulose containing biomass in a suitable container, in particular a reactor (see FIGS. 1 and 2, and as described below). As lignocellulose containing biomass, wood (hard or soft), forest trimmings, leaves, recycled paper, waste paper, paper waste, corn strover, corn fiber, wheat straw, rice straw, rye straw, sugarcane bagasse, sugar beet cuttings, switchgras, bamboo, pulp and/or similar organic materials can be used.

The lignocellulose containing material is preferably reduced in particle size to pieces of 1 cm or less and further treated e.g. it is washed and/or its water content is changed by mean known to a person of skill in the art.

As described, the first solvent which is added to the biomass in the reactor can be an inorganic acid, an inorganic hydroxide, an ionic solution, an organic acid and water or a mixture of any of these (Klemm, 1998).

The mixture of biomass and solvent(s) is preferably stirred at a temperature between 30° C. and 90° C., but the temperature need not to be constant. The pressure is at normal ambient pressure, but may be varied. After 10 to 90 minutes, at least 60% of the cellulose and hemicellulose are dissolved, depending on the kind of biomass and the first solvent used. Preferably, the incubation time is extended such that practically all of the cellulose and hemicellulose in the reactor is dissolved.

After completion of the cellulose/hemicellulose digestion as described above, the reaction is stopped using a precipitant for precipitating the cellulose and hemicellulose, thereby forming a compact solid (precipitate). A precipitant according to the invention is chosen from alkanes, ethers and/or esters or a mixture of these, which do not swell or only modestly swell cellulose. Preferably, the liquid retention value (LRV) for the precipitant is smaller than the LRV of water for the cellulose used, wherein the LRV is defined according to Klemm, 1998, page 237, as follows:

$$LRV(\%)=(\text{Mass of moist sample}-\text{Mass of dry sample})\times 100/\text{Mass of dry sample}$$

The volumetric ratio of the first solvent and the precipitant to precipitate the solid is 1:1 to 1:3, reducing the solvent amount needed for this and the following step. For this step, the conditions of temperature and pressure are considered of minor importance. Therefore, it is preferred that temperature and pressure are maintained from the previous step. Subsequently, the solid and the liquid phase are separated from each other. The solids will be further processed (see the next step, description below), whereas the first solvent and the precipitant are recovered and preferably recycled by phase separation or evaporation.

The remaining lignin can be dissolved using a second solvent, which is chosen from a ketone, an aldehyde, an alcohol, and/or water (Brauns, 1952). The volumetric ratio of the first solvent and the second solvent is preferably about 1:1. The solid and liquid phases are then separated. The solid is further processed in the next step of the method. The second solvent can be recovered by evaporation and then be recycled. The lignin precipitates as a solid and is recovered.

To further optimize the process, it is preferred that the steps using the precipitant and the second solvent be combined and performed at the same time.

Typically, the precipitate is washed with a third solvent to remove remaining traces of the first solvent, the second solvent, and/or the precipitant to achieve biocompatibility for a possible subsequent fermentation. The precipitant and the second solvent are typically recovered by distillation, whereas the first solvent is typically recovered by precipitation together with mineral salts contained in the lignocellulose containing material.

In the next step, the cellulose/hemicellulose of the precipitate is placed in a suitable reactor with a suitable buffer medium. In the reactor, the cellulose/hemicellulose is degraded to sugars and short chain sugar oligomers, either by acid hydrolysis or by enzymatic degradation using enzymes, enzyme complexes and/or a cellulolytic organism know to a person of skill in the art. Optionally, a different carbohydrate source can be added to control the sugar content of all sugars that are present in the medium as substrates, which is typically 20 g/l to 200 g/l at the outlet of this step, but can also be higher.

Subsequently, an aerobic or anaerobic fermentation using at least one kind of organism, like a bacterium or a yeast can be performed to obtain useful products like biogas (methane), hydrogen, ethanol, butanol, acetone, or similar products.

The method as described above and herein can be used for digesting a biomass comprising lignin together with cellulose and/or hemicellulose.

In another aspect, the invention pertains to an apparatus for performing a method as described above and herein.

In particular, the apparatus for performing such a method, preferably as a continuous process, comprises a first container for digesting a biomass comprising lignin, together with cellulose and/or hemicellulose, in particular a screw conveyor or a reactor, comprising a first introduction means for introducing a first solvent for dissolving the cellulose and/or the hemicellulose into the first container for contacting the biomass with the first solvent;

a second introduction means for introducing a precipitant for forming a precipitate comprising cellulose and/or hemicellulose and residual lignin into the first container for contacting the dissolved cellulose and/or hemicellulose with the precipitant; and a third introduction means for introducing a second solvent for removing residual lignin from the precipitate into the first container for contacting the precipitate with the second solvent, wherein the first, the second, and the third introduction means are arranged such as to permit a timely coordinated introduction of the first solvent, the precipitant, and the second solvent into the first container.

In a preferred embodiment of the apparatus, it further comprises a fourth introduction means for introducing a third solvent for removing residual first solvent, residual precipitant and/or residual second solvent from the precipitate into the first container for contacting the precipitate with the third solvent.

In a further aspect, the invention pertains to the use of an apparatus as described above and herein for performing a method for digesting a biomass comprising lignin together with cellulose and/or hemicellulose of the invention.

Figure 2:
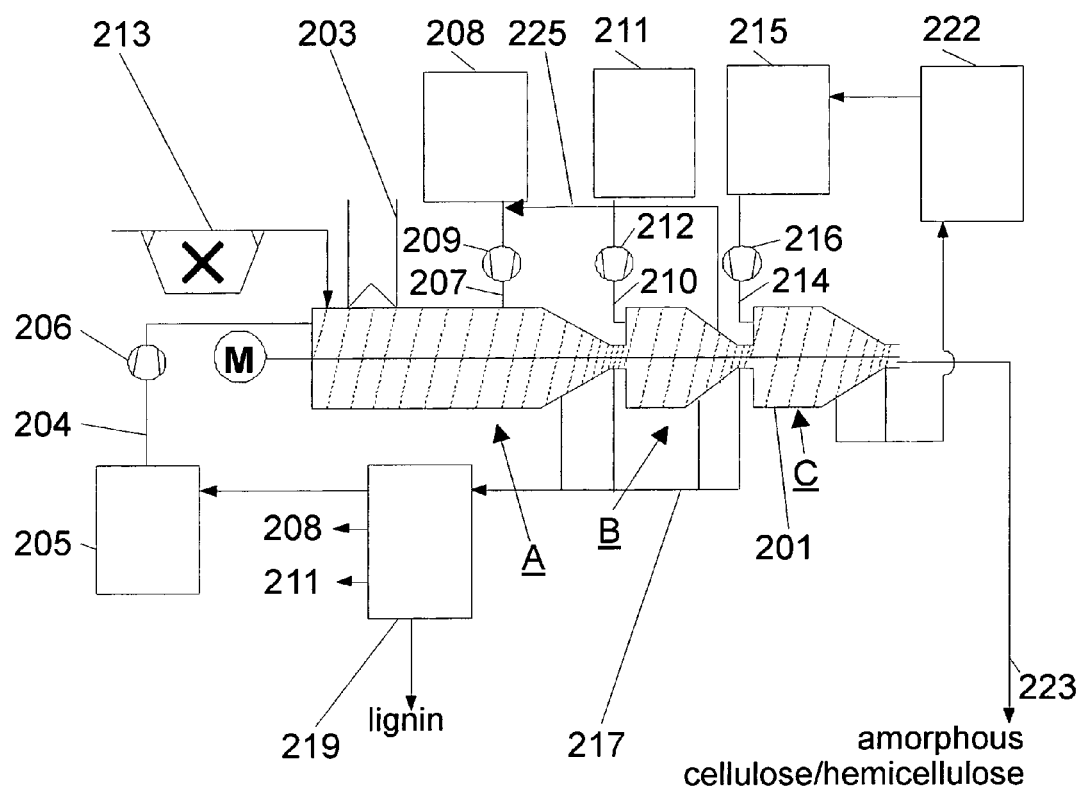
FIG. 2: Apparatus for performing the method of the invention as a continuous process. The steps of introducing the second solvent and the third solvent can also be performed in a countercurrent fashion. The step of introducing the second solvent can be combined with the step of introducing the precipitant (precipitation step).

Both FIGS. 1 and 2 show different versions of an apparatus for performing a method for adjusting a biomass comprising lignin together with cellulose and/or hemicellulose according to the present invention. FIG. 1 shows an apparatus for performing the method of the invention as batch or fed batch process, whereas FIG. 2 shows an embodiment of the apparatus for performing the method of the invention as a continuous process. In the following, aspects common to both of the embodiments of the apparatus of the invention shown in FIGS. 1 and 2 will be described with reference to both versions. For distinguishing aspects, special reference will be made to the versions shown in FIG. 1 or 2.

The different versions of the apparatus of the invention shown in FIGS. 1 and 2 both comprise a first container 101, 201 for digesting biomass comprising lignin, together with cellulose and/or hemicellulose. In the case of the versions of FIG. 1, this first container is preferably a reactor with a stirring means 102 and optionally with a heating means 103. In the case of the embodiment of FIG. 2, the first container 201 is preferably a screw conveyor possibly equipped with a heating means 203 for heating the content of the first container 201. In that case, the screw conveyor 201 comprises different compartments A, B, C (or a first compartment (A), a second compartment (B), and a third compartment (C)), wherein in each compartment a particular liquid (solvent or precipitant) is introduced to the biomass or biomass product(s). In one embodiment of the screw conveyor 201, compartment B and compartment A are identical.

In both cases, the first container 101, 201 comprises a first introduction means 104, 204, such as a pipe for introducing as first solvent for dissolving the cellulose and/or hemicellulose of the biomass into the first container 101, 201 for contacting or mixing the biomass with the first solvent. The first solvent is stored in a second container 105, 205 (a feeder tank for the first solvent) and can be introduced into the first container via the first introduction means 104, 204 using a pumping means 106, 206 such as a dosing pump.

The first container 101, 201 also comprises a second introduction means 107, 207 for introducing a precipitant for forming a precipitate comprising cellulose and/or hemicellulose and residual lignin into the first container 101, 201 for contacting or mixing the dissolved cellulose and/or hemicellulose with the precipitant in the first container 101, 201 (or, in the case of the first container being a screw conveyor 201, in compartment A of the first container 201). The precipitant is stored in a third container 108, 208 (a feeder tank for the precipitant) from which the precipitant is introduced into the first container 101, 201 through the second introduction means 107, 207 by use of a pumping means 109, 209 such as a dosing pump.

The first container 101, 201 may optionally also comprises a third introduction means 110, 210 for introducing a second solvent for removing residual lignin from the precipitate into the first container 101, 201 for contacting or mixing the precipitate in the first container 101, 201 (or, in the case of the first container being a screw conveyor 201, in compartment B of the first container 201) with the second solvent. The second solvent is introduced into the first container 101, 201 from an optional forth container 111, 211 (feeder tank for the second solvent) by use of a pumping means 112, 212 such as a dosing pump.

In the apparatus of the invention, the first introduction means 104, 204, the second introduction means 107, 207, and the third introduction means 110, 210 are arranged such as to permit a timely coordinated introduction of the first solvent, the precipitant, and the second solvent, respectively, into the first container so that the method of digesting a biomass comprising lignin together with cellulose and/or hemicellulose can be performed. Preferably, in the embodiment of FIG. 2, the first introduction means 204 is connected to the first container 201 at compartment A of the first container 201. The second introduction means 207 is preferably also connected to the first container 201 at compartment A of the first container 201, and the third introduction means 210 is connected to the first container 201 at compartment B of the first container 201.

A refeeding means 225 may be present at compartment B of the first container 201 and is arranged such that through the refeeding means 225 the precipitant can be refed from the first container 201 back into the second introduction means 207 that leads to compartment A of the first container 201. Therefore, the precipitant can be recycled due to which the amount of precipitant needed in a method of the invention is reduced. When the precipitant, possibly together with solvents (see below), is refed into the second introduction means 207, fresh precipitant may be added from the third container 208 to the recycled precipitant.

Preferably, it is not necessary to clean the precipitant that comes out of compartment B of the first container 201 before it is being introduced into compartment A of the first container 201. It is, for example, not necessary to perform a filtration and/or distillation step of the precipitant that comes out of the first container and is being refed. Although the precipitant that is being recycled is impure, the method of the present invention is not impeded by these impurities. Specifically, it is not necessary to remove any poisonous substances that might be present in the precipitant. Therefore, a removal of poisonous substances is not necessary, thereby saving an additional method step rendering the method of the present invention performed by such an apparatus less costly and less energy consuming compared to the state of the art.

As shown in FIG. 2, it is most preferred that the refeeding means 225 is configured to reintroduce the first solvent, the precipitant, and the second solvent back into the first container 201. It was shown by the inventor that this reintroduction can be performed without the need for laborious separation steps of the precipitant from the solvents. This leads to savings in energy and chemicals, thereby reducing costs.

In order for the biomass that is introduced into the first container 101, 201 to be of the appropriate size, a means for reducing the size of the biomass 113, 213 (such as a chopping or grinding device) can be arranged separately or as an integral part of the apparatus.

In addition, the apparatus may further comprise a forth introduction means 114, 214 for introducing a third solvent for removing residual first solvent, residual precipitant, and/or residual second solvent from the precipitate into the first container 101, 201 (or, in the case of the first container being a screw conveyor 201, into compartment C of the first container 201) for contacting the precipitate with the third solvent therein. The third solvent is introduced into the first container 101, 201 via the forth introduction means from a fifth container 115, 215 by use of a pumping means 116, 216 such as a dosing pump.

In the embodiment shown in FIG. 1, a first release means 117 such as a pipe is located preferably at the bottom of the first container 101 which can be controlled though a controlling means 118 such as a valve to recover the first solvent, the precipitant, and/or the second solvent into a sixth container 119. From this sixth container 119, the lignin can be recovered.

From the sixth container 119 the recovered liquids can be reintroduced into the respective container (feeder tank) 105, 108, 111, namely the first solvent into the second container 105, the precipitant into the third container 108, and the second solvent into the fourth container 111.

The first container 101 also has a second release means 120 such as a pipe controlled by a controlling means 121 such as a valve for releasing the third solvent into a seventh container 122 for recovering the third solvent, from where it can be recycled into the fifth container 115, which is the feeder tank for the third solvent for the first container 101. The fifth container 115 is connected with the seventh container 122 through a connection means 123. Due to this arrangement, the third solvent can be recycled. The mineral salts contained in the lignocellulosic material used can be recovered from the seventh container 122.

Through a third release means 124, the (amorphous) cellulose/hemicellulose can be released from the first container 101 through a third controlling means 125 such as a valve.

In the embodiment shown in FIG. 2, a sixth container 219 for recovering the first solvent, the precipitant, and the second solvent is present and is connected with compartments A and B of the first container 201 through a release means 217, e.g. in the form of a pipe or pipes which can comprise controlling means for controlling the release of liquids from compartment C of the first container 201. The recovered first or second solvent or the recovered precipitant can be reintroduced into the respective container, namely into the second container 205 (feeder tank) for the first solvent, into the third container 208 for the precipitant, and for the fourth container 211 for the second solvent. The first and second solvent and the precipitant are thereby recycled. From the sixth container 219, the lignin can be recovered.

The third solvent can be recovered into a seventh container 222 from which the third solvent can be reintroduced into the fifth container 215, which is the feeder tank for the first container 201 (compartment C). The mineral salts contained in the lignocellulose containing material used can be recovered from the seventh container 222.

The (amorphous) cellulose/hemicellulose can be released from the first container 201 (screw conveyor, compartment C) through a release means 223.

EXAMPLES

Example 1

Lignocellulose containing biomass in the form of 600 mg of coarsely grained wheat straw was stirred with 5 ml 80% $H_3PO_4$ as a first solvent at 55° C. for 35 min to the complete solution of the straw. The black viscous medium was cooled to approx. 40° C. and then mixed vigorously with 10 ml of pre-cold MtB ether as a precipitant to give a compact precipitate of cellulose/hemicellulose. The solid phase (the precipitate) was washed with 5 ml MtB ether as a third solvent to remove residual $H_3PO_4$. The MtB ether was recovered by distillation.

The precipitate was mixed vigorously with 5 ml acetone as a second solvent and then centrifuged. This was repeated once again. The supernatant was collected and the acetone was recycled by distillation. Moreover, the lignin was recovered.

The solid phase was washed 2 times with 5 ml distilled water as a third solvent to remove remaining $H_3PO_4$ (first solvent), MtB ether (precipitant) and acetone (second solvent). The precipitate remains as a light brown solid, which is readily fermented by the Trichoderma enzyme (50° C. 10 g/l glucan and 10 FPU/g glucan).

Example 2

Lignocellulose containing biomass in the form of 1 g of crushed leaves were mixed with 7.5 ml 80% $H_3PO_4$ as a first solvent and stirred at 50° C. for 40 min. The solution is precipitated with 12 ml pre-cold mixture of ETBE/acetone (ETBE=ethyl-tert. butylether, EtB ether) as precipitant with a ratio of 3:1. The solid phase (the precipitate) was separated by centrifugation and the supernatant was collected. The acetone was distilled from the supernatant and recycled. The remaining liquid readily forms two phases and the clear brown organic phase was removed. The ETBE of the organic phase was removed by distillation and 80 mg of lignin were recovered.

The solid phase containing cellulose and hemicellulose was washed 2 times with 5 ml distilled water as a third solvent to remove remaining $H_3PO_4$ (first solvent), EtB ether (precipitant) and acetone (second solvent). It remains a light brown solid, which is readily fermented by the Trichoderma enzyme (50° C. 10 g/l glucan and 10 FPU/g glucan).

Example 3

Precipitation Experiments

Precipitation Experiments for cellulose and hemicellulose from a solution of phosphoric acid ($H_3PO_4$) as a first solvent were performed using different precipitants. These precipitants known in the state of the art for this purpose include acetone and ethanol. The precipitants according to the present invention that were used are MtB-ether, pentane, and ethyl acetate (see table 1).

2 ml of a solution of phosphoric acid/lignocellulose (0.15 g lignocellulose/ml) were mixed with 15 ml of a precipitant as shown in table 1 and subsequently centrifuged for 15 minutes at 5000 rpm in a table centrifuge. The supernatant was discarded and both the volume and the weight of the precipitate were measured.

TABLE 1

| Precipitant | Volume of the precipitate (ml) | Weight of the precipitate (g) | Weight of the precipitate/ Weight of the lignocellulose |
|---|---|---|---|
| Acetone | 3.5 | 3.610 | ~12 |
| Ethanol | 4 | 3.920 | ~13 |
| MtB-Ether | <1 | 0.890 | ~3 |

TABLE 1-continued

| Precipitant | Volume of the precipitate (ml) | Weight of the precipitate (g) | Weight of the precipitate/ Weight of the lignocellulose |
|---|---|---|---|
| Ethyl acetate | <1 | 0.770 | ~2.5 |
| Pentane | 1.8 | 1.930 | ~6.5 |

As can be seen from the results shown in table 1, the precipitate resulting form a precipitation with ethanol or acetone as a precipitant was heavier than the precipitates obtained by a precipitation with acetone or ethanol. This shows that more of the precipitant remains in the precipitate in case of a precipitation with ethanol or acetone as compared to other precipitants, since in all cases, about 250 mg to 300 mg cellulose and hemicellulose were precipitated.

Example 4

Precipitation Experiments from $H_3PO_4$ Solution

Figure 3:
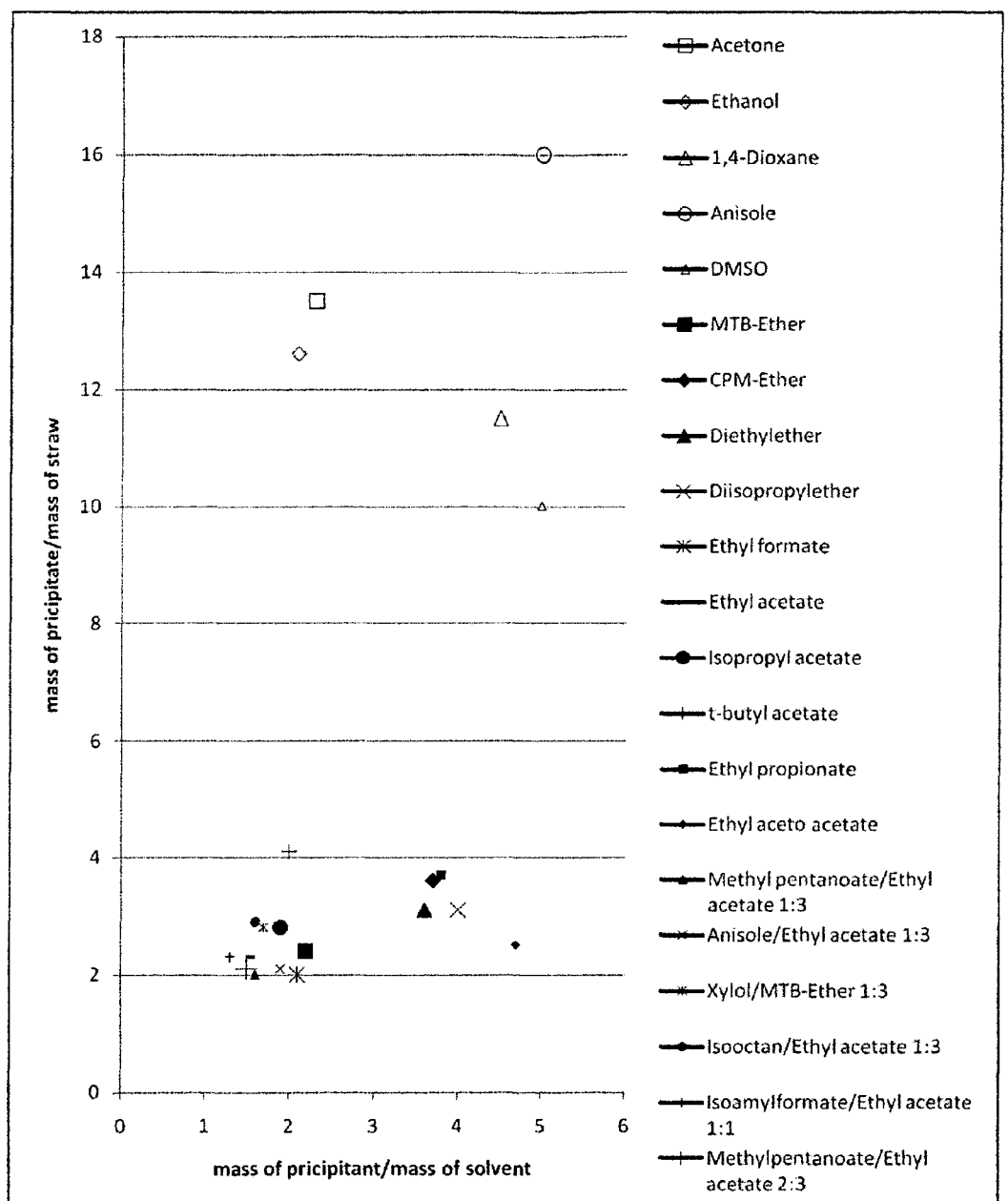
FIG. 3: Shown are the results of the precipitation experiments. Open symbols represent precipitants known in the state of the art. Closed symbols represent precipitants according to the present invention.

Precipitation Experiments for cellulose and hemicellulose from a solution of phosphoric acid ($H_3PO_4$) as a first solvent were performed using different precipitants. Precipitants known in the state of the art for this purpose include acetone and ethanol. In control experiments, anisole, DMSO and 1,4-dioxane were used as precipitants. The precipitants according to the present invention that were used are MtB-ether, cyclopentyl methyl ether (CPME), diisopropyl ether, ethyl aceto acetate, isooctane, xylol, ethyl acetate, propyl acetate, ethyl propionate, isopropyl acetate, t-butyl acetate, methyl pentanoate, isoamyl formate, ethyl formate and different mixtures there of (see table 2 and FIG. 3).

2.5 g of a solution of phosphoric acid/lignocellulose (0.109 g lignocellulose/g) were mixed with different amounts of a precipitant as shown in table 2 and subsequently centrifuged for 15 minutes at 5000 rpm in a table centrifuge. The supernatant was discarded and the weight of the precipitate was measured as an indicator for residual precipitant in the precipitate.

TABLE 2

Results of the precipitation experiments from $H_3PO4$ solution with different precipitants.

| Precipitant | Mass of precipitant/ mass of solvent | Mass of the precipitate/ mass of the lignocellulose |
|---|---|---|
| Acetone | 2.3 | 13.5 |
| Ethanol | 2.1 | 12.6 |
| 1,4-Dioxane | 4.5 | 11.5 |
| Anisole | 5 | ~16 |
| DMSO | 5 | ~10 |
| MTB-Ether | 2.2 | 2.4 |
| CPM-Ether | 3.7 | 3.6 |
| Diethylether | 3.6 | 3.1 |
| Diisopropylether | 4 | 3.1 |
| Ethyl formate | 2.1 | 2.0 |
| Ethyl acetate | 1.5 | 2.3 |
| Propyl acetate | 1.9 | 2.7 |
| Isopropyl acetate | 1.9 | 2.8 |
| t-butyl acetate | 2.0 | 4.1 |
| Ethyl propionate | 3.8 | 3.7 |
| Ethyl aceto acetate | 4.7 | 2.5 |
| Methyl pentanoate/ Ethyl acetate 1:3 | 1.6 | 2.0 |
| Methylpentanoate/Ethyl acetate 2:3 | 1.5 | 2.1 |
| Anisole/Ethyl acetate 1:3 | 1.9 | 2.1 |
| Xylol/MTB-Ether 1:3 | 1.7 | 2.8 |
| Hexane/MTB-Ether 1:3 | 1.8 | 2.7 |
| Isooctan/Ethyl acetate 1:3 | 1.6 | 2.9 |
| Isoamylformate/Ethyl acetate 1:1 | 1.3 | 2.3 |

Example 5

Fermentation Experiments

Fermentation experiments are carried out to show that bacteria are not inhibited by the pretreated substrate either due to residual solvent or to precipitant of the pretreatment, i.e. the digestion procedure or by a toxic substance (such as furfural) that might have formed during the pretreatment procedure. This shows directly that no laborious or expensive detoxification step is necessary in the pretreatment procedure. For the fermentation experiments, the amount of substrate corresponding to 0.25 g dry biomass was given into a gas tied flask with 150 ml biogas digestate as inoculum to start the biogas production and 50 ml of water. Subsequently, the gas production was measured.

Furthermore, the biogas production of 150 ml biogas digestate and 50 ml water without any further substrate was measured as the blank test. The produced biogas volume after 25 days of fermentation normalized to standard conditions (pressure p=101.325 kPa and temperature T=273.15 K) and 1 kg dry biomass are given in table 3.

The substrate preparation was as follows: For every type of biomass (wheat straw, corn silage and the solid part of the biogas digestate) a stock solution of 10 g dry biomass and 50 ml 85% $H_3PO_4$ was prepared at 55° C. to 60° C.

Preparation Method a)

10 g of the stock solution was precipitated with 20 g of MTB ether and filtered thereafter. The filter cake was washed with another 20 g of MTB ether. Subsequently, the filter cake was washed two times with 25 ml hot water to remove residual MTB ether. The resulting substrate corresponds to 1.05 g of dry biomass.

Preparation Method b)

10 g of the stock solution was precipitated with a 20 g of a mixture of 50 MTB ether and 50% acetone and filtered thereafter. The filter cake was washed with the another 20 g of the mixture and in the following with two time 25 ml of hot water to remove the residual mixture. The resulting substrate corresponds to 1.05 g of dry biomass.

Preparation Method c)

10 g of the stock solution was precipitated with a 20 g of a mixture of ethyl formate and filtered thereafter. The filter cake was washed with the another 20 g of ethyl formate and in the following with two time 25 ml of hot water to remove the residual ethyl formate. The resulting substrate corresponds to 1.05 g of dry biomass.

The results show that bacteria are not inhibited by the different preparation methods a), b) and c) as described above.

TABLE 3

Results of the fermentation experiments already adjusted for the blank test (i.e. the value obtained for a control without substrate was subtracted from the values obtained for the samples). Nl refers to a norm liter, i.e. a gas volume that was calculated to refer to standard conditions as defined above.

| Substrate/Stock solution | Preparation method | Biogas production after 25 days (Nl/kg dry biomass) |
|---|---|---|
| Wheat straw | None | 270-310 |
| Wheat straw | a) | 550 |
| Wheat straw | b) | 565 |
| Wheat straw | c) | 580 |
| Corn silage | None | 670 |
| Corn silage | b) | 1100 |
| Solid part of biogas digestate of Corn silage | None | 0 |
| Solid part of biogas digestate of Corn silage | c) | 720 |

Example 6

Precipitation Experiments from the Ionic Liquid DMA/LiCl

Precipitation experiments for cellulose and hemicellulose from a solution of DMA/LiCl as a first solvent and an example of an ionic liquid were performed using different precipitants. These precipitants known in the state of the art for this purpose include acetone and ethanol. The precipitants according to the present invention that were used in this example are MtB-ether, benzene, toluene, pentane, isoamyl formate, and methyl pentanoate.

2.5 g of a solution of DMA/LiCl/lignocellulose (0.05 g lignocellulose/g) were mixed with different amounts of a precipitant as shown in table 4 and subsequently centrifuged for 15 minutes at 5000 rpm in a table centrifuge. The supernatant was discarded and the weight of the precipitate was measured.

TABLE 4

Results of the precipitation experiments from DMA/LiCl as an example of an ionic liquid with different precipitants.

| Precipitant | Mass of precipitant/ mass of solvent | Mass of the precipitate/ mass of the lignocellulose |
|---|---|---|
| Acetone | 1.7 | 15 |
| Ethanol | 2.0 | 10.5 |
| Benzene | 1.5 | 3.5 |
| Toluene | 1.6 | 3.1 |
| Toluene/pentane 1:1 | 1.7 | 2.8 |
| MTB-ether | 2.2 | 4.1 |
| Isoamyl formate | 1.8 | 2.5 |
| Methyl pentanoate | 1.6 | 2.7 |

REFERENCES

Klemm, 1998: Klemm, D., Philipp, B., Heinze, T., Heinze, U., Wagenknecht, U. Comprehensive Cellulose Chemistry Vol. I, Weinheim, VCH-Wiley 1998

Brauns, 1952: Brauns, F. E. The Chemistry of Lignin, New York, Academic Press 1952

REFERENCE LISTING 101, 201 first container
102 stirring means
103 heating means
104, 204 first introduction means
105, 205 second container
106, 206 pumping means
107, 207 second introduction means
108, 208 third container
109, 209 pumping means
110, 210 third introduction means
111, 211 forth container
112, 212 pumping means
113, 213 means for reducing the size of the biomass
114, 214 fourth introduction means
115, 215 fifth container
116, 216 pumping means
117 first release means
118 controlling means
119 sixth container
120 second release means
121 controlling means
122 seventh container
123 connection means
124 third release means
125 third controlling means
219 sixth container
222 seventh container
223 release means
225 refeeding means.

The invention claimed is:

1. A method for digesting a biomass comprising lignin together with at least one of cellulose and hemicellulose, comprising the steps of:
   (a) contacting the biomass with a first solvent for selectively dissolving at least one of the cellulose and the hemicellulose;
   (b) contacting at least one of the dissolved cellulose and the dissolved hemicellulose with a precipitant for forming a precipitate comprising at least one of the cellulose and the hemicellulose and wherein the precipitate includes a residual lignin, wherein the precipitant is selected from the group consisting of MTB-ether, CPM-ether, diethylether, diisopropylether, ethyl formate, ethyl acetate, propyl acetate, isopropyl acetate, t-butyl acetate, ethyl propionate, ethyl aceto acetate, methyl pentanoate/ethyl acetate 1:3, methylpentanoate/ethyl acetate 2:3, anisole/ethyl acetate 1:3, xylol/MTB-ether 1:3, hexane/MTB-ether 1:3, isooctane/ethyl acetate 1:3, isoamylformate/ethyl acetate 1:1, and mixtures; and
   (c) contacting the precipitate with a second solvent for removing the residual lignin from the precipitate.

2. The method according to claim 1, wherein step (b) is performed at the same time as step (c).

3. The method according to claim 1, further comprising the step of
   (d) contacting the precipitate with at least one of a third solvent for removing residual first solvent, residual precipitant and residual second solvent from the precipitate.

4. The method according to claim 3, further comprising the steps of
   (e) contacting the precipitate with a fourth solvent for performing at least one of dissolving and resuspending at least one of the cellulose and the hemicellulose, wherein the fourth solvent is selected from a group consisting of water and buffer solutions; and (f) performing an aerobic fermentation or anaerobic fermentation on at least one of the cellulose, the hemicellulose, and the lignin.

5. The method according to claim 1, wherein the first solvent is selected from the group consisting of an inorganic acid; an inorganic hydroxide; an organic acid;
an ionic solution; a solution of at least one transition metal complex;
water; and any mixture thereof.

6. The method of claim 5, wherein the inorganic acid is selected from the group consisting of sulfuric acid, hydrochloric acid, nitric acid, phosphoric acid, and polyphosphoric acid, wherein the organic acid is selected from the group consisting of formic acid, acetic acid, propionic acid, butyric acid, ammonia, and hydrazine;
and wherein the inorganic hydroxide is selected from the group consisting of potassium hydroxide, sodium hydroxide, and lithium hydroxide.

7. The method according to claim 1, wherein the second solvent is selected from the group consisting of a ketone with 7 C-atoms or less; an alcohol; an aldehyde; water; and any mixture thereof.

8. The method of claim 7, wherein the ketones are selected from the group consisting of dipropylketone, ethyl-butyl-ketone, methyl-pentyl-ketone, ethyl-propyl-ketone, methyl-butyl-ketone, diethylketone, methyl-propyl-ketone, methyl-ethyl-ketone, acetone, and isomers thereof, wherein the alcohols are selected from the group consisting of hexanol, pentanol, butanol, propanol, ethanol, methanol and isomers thereof and wherein the aldehydes are selected from the group consisting of hexanal, pentanal, butanal, propanal, ethanal and isomers thereof.

9. The method according to claim 3, wherein the third solvent is selected from the group consisting of
water, and
a saturated hemicellulose solution.

10. The method according to claim 1, wherein the ratio of the first solvent to the biomass is at least about 5:1 (w/w).

11. The method according to claim 1, wherein the volumetric ratio of the first solvent to the precipitant is from about 1:1 to about 1:3 (vol/vol).

* * * * *